United States Patent [19]
Cavazza et al.

[11] Patent Number: 5,614,556
[45] Date of Patent: Mar. 25, 1997

[54] L-CARNITINE SALT AND COSMETIC AND PHARMACEUTICAL COMPOSITIONS CONTAINING SAME FOR TREATING DERMATOSES

[75] Inventors: Claudio Cavazza; Paolo Cavazza, both of Rome, Italy

[73] Assignee: Avantgarde S.p.A., Rome, Italy

[21] Appl. No.: 473,211

[22] Filed: Jun. 7, 1995

[30] Foreign Application Priority Data

Sep. 8, 1994 [IT] Italy .................. RM94A0571

[51] Int. Cl.⁶ .................. A61K 31/205; C07C 229/00
[52] U.S. Cl. .................. 514/556; 562/567
[58] Field of Search .................. 562/567

[56] References Cited

U.S. PATENT DOCUMENTS 5,498,633  3/1996  Santaniello et al. .................. 514/547

Primary Examiner—Paul J. Killos
Attorney, Agent, or Firm—Oblon, Spivak, McClelland, Maier & Neustadt, P.C.

[57] ABSTRACT

L-carnitine trichloroacetate and its use for producing cosmetic and pharmaceutical compositions suitable to be topically applied for the treatment of dermatoses, are disclosed.

17 Claims, No Drawings

L-CARNITINE SALT AND COSMETIC AND PHARMACEUTICAL COMPOSITIONS CONTAINING SAME FOR TREATING DERMATOSES

The present invention relates to a novel L-carnitine salt and the use thereof for producing cosmetic and pharmaceutical compositions which contain such salt, suitable to be topically applied for the treatment of dermatoses.

This novel L-carnitine salt is L-carnitine trichloroacetate of formula (I)

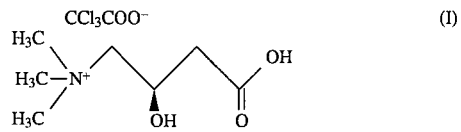

L-carnitine trichloroacetate is a highly stable and non-hygroscopic salt. This is quite surprising since trichloroacetic acid is an extremely deliquescent compound. Surprising as well is the activity of this novel salt in the dermatologic field since trichloroacetic acid exhibits a caustic and revulsive vesicant action.

In the following example the preparation of L-carnitine trichloroacetate is described.

EXAMPLE

Preparation of L-carnitine trichloroacetate (ST 1162) L-carnitine inner salt (16.1 g; 0.1 moles) was dissolved in 100 mL $H_2O$. To the resulting solution, trichloroacetic acid (16.4 g; 0.1 moles) dissolved in 100 mL $H_2O$, was added.

The resulting solution was concentrated under vacuum at 40°. The solid residue which formed was taken up with acetone and the solid filtered off. 31 g of the title compound were obtained. The compound was crystallized from hot isopropanol. Melting Point 79,3° C. (DSC).

The compound was stable and non-hygroscopic.

| Elementary analysis: $C_9H_{16}NO_5Cl_3$ | | | | |
|---|---|---|---|---|
| | C % | H % | N % | Cl % |
| calculated | 33.30 | 4.96 | 4.31 | 32.77 |
| found | 33.32 | 5.09 | 4.36 | 32.69 |

$H_2O$ content 1.1% pH=2.8, $H_2O$ $[\alpha]_D^{25}$=15,1° (c=1%, $H_2O$ )

HPLC column: (L-carnitine) μ Bondapak-$NH_2$ (10 μm) 300 mm×3,9 mm Temperature: 30° C. mobilephase: $CH_3CN/KH_2PO_4$ 50 mM pH 5,2 65/35 Flow-rate: 1,0 ml/min L-carnitine: $R_t$=8,21 min 51,9% Column: (trichloroacetic acid) IONPAC-AS4A/SC Eluant: NaOH 50 mM Flow-rate: 1,0 ml/min room temperature Trichloroacetic acid Rt=6,06 min 48,4%

NMR $D_2O$ δ4.5–4.4 (1H,m, C$\underline{H}$OH); 3.3 (2H, m, $CH_2$N+ ); 3.1 (9 h, s,$(CH_3)_3$N+); 2.5(2H,dd,$CH_2$COO)

L-carnitine trichloroacetate is used as active ingredient for producing cosmetic and dermatologic pharmaceutical compositions suitable to be topically applied.

The dermatoses which are suitably treated with the compositions of the present invention are in particular ichthyosis, psoriasis and those dermatoses which are induced by a defective keratinization, such as dandruff, acne and palmar and plantar hyperkeratosis.

Ichthyosis is a dermatosis characterized by generalized dryness, harshness and scaling of the skin. It may occur as a hereditary disease present at birth, or as a metabolic disorder associated with hypothyroidism or with the intake of drugs (such as butyrophenols) inhibiting lipid synthesis, or as a paraneoplastic syndrome, manifestation of a tumor process involving internal organs.

Xeroderma, the mildest form of ichthyosis is neither congenital nor associated with systemic abnormalities. It usually occurs on the lower legs of middle-aged or older patients, most often in cold weather and in patients who bathe frequently. There may be mild to moderate itching and an associated dermatitis due to detergents or other irritants.

The inherited ichthyoses, all characterized by excessive accumulation of scale on the skin surface, are classified according to clinical, genetic, and histologic criteria.

Known treatments of any form of ichthyosis comprise topically applying to the skin hydrating emollients. Furthermore, salicylic acid or vitamin A-containing ointments have been widely used.

A keratolytic agent particularly effective in removing the scale in ichthyosis vulgaris, lamellar ichthyosis and sex-linked ichthyosis contains 6% salicylic acid in a gel composed of propylene glicol, ethyl alcohol, hydroxypropylene cellulose and water.

Further known drugs for the the treatment of this disorder include: 50% propylene glicol in water, hydrophilic petrolatum and water (in equal parts), and cold cream and an a-hydroxy acid (e. g. lactic and pyruvic acid) in various bases. In lamellar ichthyosis, 0.1% tretinoin (vitamin A acid; retinoic acid) cream has been utilizad. None of these treatments has been found satisfactorily effective.

Hyperkeratosis is a thickening of the stratum corneum of the skin.

The treatment of choice is the topical application of drugs containing urea, propylene glycol or salicylic acid. Also in this case, none of the known treatment has proved to be satisfactorily effective.

It has now been found that the compound of the present invention, when topically applied as solutions, lotions, creams of ointments containing from 0,01% to 20%, preferably from 1% to 15% and most preferably from 2 to 10% by weight of at least one of the foregoing compounds, are potently effective in achieving complete remission of ichthyotic conditions in humans and in healing psoriasis and those disorders brought about by an altered keratinization, such as danddruff, acne and palmer and plantar hyperkeratosis. It has also been found that, if the solutions, creams or ointments of the invention are applied regularly on a daily basis, within about two to three weeks the effected skin areas will return to normal conditions.

In order to prepare the compositions of this invention, L-carnitine trichloroacetate is preferably dissolved in water or ethanol initially. The solution thus prepared may be admixed in the conventional manner with commonly available ointment bases such as hydrophilic ointment (USP) or petrolatum (USP).

The water or ethanol used to dissolve the compounds according to this invention may range in concentration of from 1 to 30%, by volume, of the total composition. The compounds of this invention may also be formulated in a solution or lotion form.

For istance, an ester according to the invention is dissolved directly in a mixture of water, ethanol and propylene glicol (40:40:20 by weight).

Some examples of the formulation are herein below described:

Formulation 1:5% solution 5 grams of the salt were dissolved in 5 mL of water and the resulting solution admixed with 40 mL of ethanol and 20 mL of propylene glicol. Sufficient water was added to make 100 mL of formulation.

Formulation 2:5% ointment 5 grams of the salt were admixed with 95 grams of USP grade hydrophilic ointment, until an uniform consistence resulted.

We claim:

1. L-carnitine trichloroacetate of formula (I)

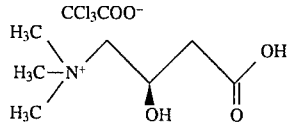

2. A pharmaceutical composition, which comprises (A) the compound of formula (I):

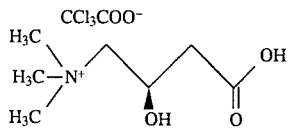

and (B) a pharmacologically acceptable carrier.

3. The composition of claim 2, for treating ichthyosis and psoriasis.

4. The composition of claim 2 for treating dermatoses brought about by defective keratinization.

5. The composition of claim 4, for treating dandruff, acne and palmar and plantar hyperkeratosis.

6. The composition of claim 2, which is in the form of a solution, lotion, ointment, or cream.

7. The composition of claim 6, which comprises from 0.1% to 20% by weight of said compound of formula (I).

8. The composition of claim 6, which comprises from 1% to 15% by weight of said compound of formula (I).

9. The composition of claim 6, which comprises from 2% to 10% by weight of said compound of formula (I).

10. A method for treating dermatosis, which comprises topically administering an effective amount of the compound of formula (I):

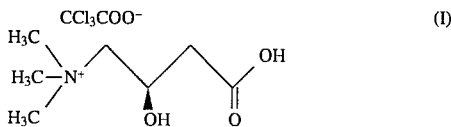

to a patient in need thereof.

11. The method of claim 10, wherein said dermatosis is selected from the group consisting of ichthyosis and psoriasis.

12. The method of claim 10, wherein said dermatoses is brought about by defective keratinization.

13. The method of claim 12, wherein said dermatosis is selected from the group consisting of dandruff, acne and palmar and plantar hyperkeratosis.

14. The method of claim 10, wherein said compound of formula (I) is applied in a composition in the form of a solution, lotion, ointment or cream.

15. The method of claim 14, wherein said composition comprises from 0.1% to 20% by weight of said compound formula (I).

16. The method of claim 14, wherein said composition comprises 1% to 15% by weight of said compound of formula (I).

17. The method of claim 14, wherein said composition comprises 2% to 10% by weight of said compound of formula (I).

* * * * *